US006377841B1

(12) United States Patent
Lin et al.

(10) Patent No.: US 6,377,841 B1
(45) Date of Patent: Apr. 23, 2002

(54) TUMOR DEMARCATION USING OPTICAL SPECTROSCOPY

(75) Inventors: Wei-Chiang Lin; Anita Mahadevan-Jansen; E. Duco Jansen; Steven A. Toms, all of Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 09/545,425

(22) Filed: Apr. 7, 2000

Related U.S. Application Data

(60) Provisional application No. 60/193,491, filed on Mar. 31, 2000.

(51) Int. Cl.[7] .................................................. A61B 6/00
(52) U.S. Cl. ........................ 600/477; 600/478; 356/303
(58) Field of Search ........................ 600/407, 473–478; 356/302, 303, 341, 342

(56) References Cited

U.S. PATENT DOCUMENTS

| 4,768,513 | A | * | 9/1988 | Suzuki ........................ 600/476 |
| 4,786,813 | A | | 11/1988 | Svanberg et al. |
| 4,930,516 | A | | 6/1990 | Alfano et al. |
| 4,957,114 | A | | 9/1990 | Zeng et al. |
| 5,042,494 | A | | 8/1991 | Alfano |

(List continued on next page.)

FOREIGN PATENT DOCUMENTS

| WO | WO 90/12536 | 11/1990 |
| WO | WO 93/03672 | 3/1993 |
| WO | WO 99/01749 | 1/1999 |
| WO | WO 99/02956 | 1/1999 |
| WO | WO 99/17668 | 4/1999 |
| WO | WO 99/18847 | 4/1999 |

OTHER PUBLICATIONS

Bottiroli et al., "Brain Tissue Autofluorescence: An Aid for Intraoperative Delineation of Tumor Resection Margins," journal art., *Cancer Detection and Prevention*, 22 (4), pp. 330–339, Aug., 1998, Int'l. Soc. for Preventive Oncology, UMASS Med. Center, Worcester, MA.

Lin et al. "Spectroscopic–guided Free–Electron Lasaer (FEL) Ablation of Brain Tissue", slide presentation at FEL Workshop, cover and pp. 1–7 (13 slides), Jun. 13, 1998, Boston, MA.

Lin et al., "Fluorescence and Reflectance Spectroscopy in Brain Tumor Margin Detection", journal art. *Bulletin of the Stefan University*, vol. 11, No. 14, pp. 235–236, Apr., 1999, Stefan Univ, La Jolla, CA.

(List continued on next page.)

*Primary Examiner*—Marvin M. Lateef
*Assistant Examiner*—Shawna J Shaw
(74) *Attorney, Agent, or Firm*—Akin, Gump, Strauss, Hauer & Feld, L.L.P.

(57) ABSTRACT

Optical spectroscopy for brain tumor demarcation was investigated in this study. Fluorescence and diffuse reflectance spectra were measured from normal and tumorous human brain tissues in vitro. A fluorescence peak was consistently observed around 460 nm (±10 nm) emission from both normal and tumorous brain tissues using 337 nm excitation. Intensity of this fluorescence peak ($F_{460}$) from normal brain tissues was greater than that from primary brain tumorous tissues. In addition, diffuse reflectance (Rd) between 650 nm and 800 nm from white matter was significantly stronger than that from primary and secondary brain tumors. A good separation between gray matter and brain tumors was found using the ratio of $F_{460}$ and Rd at 400 nm–600 nm. Two empirical discrimination algorithms based on F (400 nm–600 nm), Rd (600 nm–800 nm), and F (400 nm–600 nm)/Rd (400 nm–600 nm) were developed. These algorithms yielded an average sensitivity and specificity of 96% and 93%, respectively.

20 Claims, 3 Drawing Sheets

U.S. PATENT DOCUMENTS

| | | | |
|---|---|---|---|
| 5,131,398 A | | 7/1992 | Alfano et al. |
| 5,421,339 A | * | 6/1995 | Ramanujam et al. ....... 600/476 |
| 5,452,723 A | | 9/1995 | Wu et al. |
| 5,474,909 A | | 12/1995 | Connors et al. |
| 5,566,673 A | | 10/1996 | Shiono et al. |
| 5,582,168 A | * | 12/1996 | Samuels et al. ............ 600/407 |
| 5,590,660 A | | 1/1997 | MacAulay et al. |
| 5,623,932 A | * | 4/1997 | Ramanujam et al. ....... 600/476 |
| 5,687,730 A | * | 11/1997 | Dorion et al. .............. 600/477 |
| 5,697,373 A | * | 12/1997 | Richards-Kortum et al. .......................... 600/473 |
| 5,735,276 A | | 4/1998 | Lemelson |
| 5,827,190 A | | 10/1998 | Palcic et al. |
| 6,069,689 A | * | 5/2000 | Zeng et al. ................... 356/73 |
| 6,091,985 A | * | 7/2000 | Alfano et al. ............... 600/476 |
| 6,095,982 A | * | 8/2000 | Richards-Kortum et al. .......................... 600/476 |
| 6,128,525 A | * | 10/2000 | Zeng et al. ................. 600/476 |

OTHER PUBLICATIONS

Lin et al., "Spectroscopic–guided Free–Electron Laser Ablation of Human Brain Tissue", Abstract for Gordon Research Conference, 1 page, Jun., 1998, Meriden, NH.

"Motivation", Powerpoint presentation for Gordon Research Conference, 13 pp, Jun., 1998, Meriden, NH.

"Motivation", Powerpoint presentation, Nashville, TN, 12 pp., Aug., 1998, Nashville, TN.

Toms et al., Potential of Optical Spectroscopy in Brain Tumor Margin Delineation, Abstr submittede to 1999 Congress of Neurosurgeons, 2 pp., Oct. 30, 1999, Boston, MA.

Lin et al., "Fluorescence and Reflectance Spectroscopy in Brain Tumor Margin Detection", Abstr to 1999 Laser Medicine and Biophysics Conference, 1 page, Apr. 19, 1999, La Jolla, CA.

Lin et al., "Optical Spectroscopy for Brain Tumor Margin Detection", Powerpoint presentation at 1999 Tennessee Bio-Medical Engineering Conference, 32 pp., Apr. 9, 1999, Nashville, TN.

Lin et al., Optical Spectroscopy in Brain Tumor Martin Detection, Internet website abstr. for the 1999 Tennessee BME Conference, 1 page, Internet pub before Mar. 31, 1999, USA.

Lin et al., "Optical spectroscopy for intra–operative guidance of brain tumor resection", Abstr for 2000 OSA Meeting, 3 pp, Apr., 2000, Miami, FL.

* cited by examiner

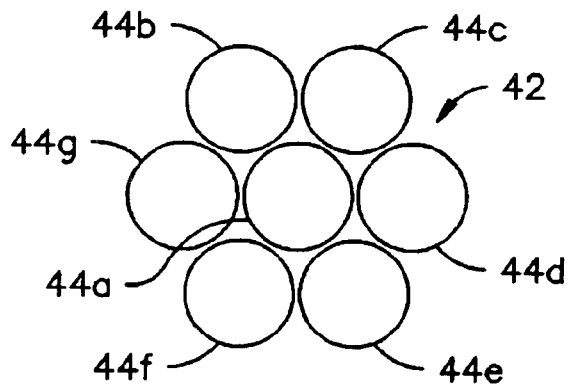
*Fig. 2a*
*Fig. 2b*
*Fig. 2c*
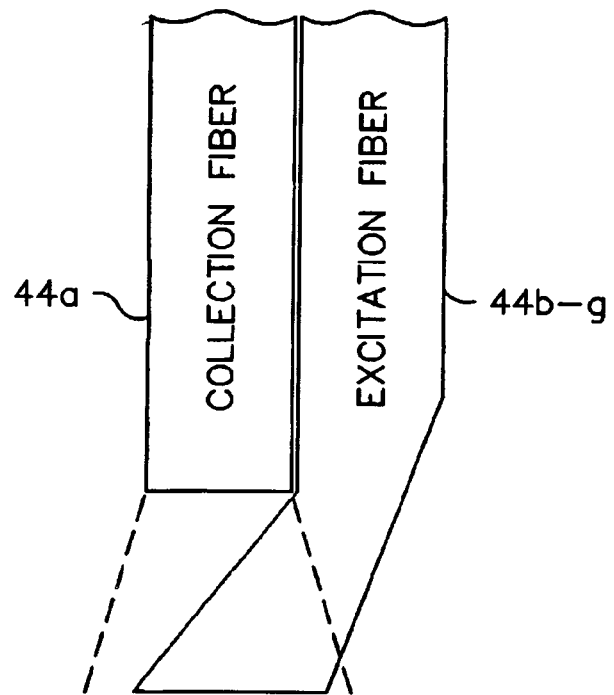

TUMOR DEMARCATION USING OPTICAL SPECTROSCOPY

CROSS REFERENCE TO RELATED APPLICATIONS

This application claims the benefit of U.S. Provisional Patent Application No. 60/193,491 filed Mar. 31, 2000 (Express Mail Label No. EL474253966US) and entitled "Tumor Demarcation Using Optical Spectroscopy", the subject matter of which is incorporated herein by reference.

BACKGROUND OF THE INVENTION

Cancer is a significant cause of illness-related deaths in the United States. It is estimated that approximately 17,000 malignant brain tumors are diagnosed in adults and 1,500 in children every year in the United States.

Brain tumors are usually lethal. Human brain tumors are typically classified as primary tumors and secondary tumors depending on their origin 1. Primary tumors originate in the brain and are classified according to the histological basis from which they are derived; for example, gliomas arise from glial tissue. Secondary tumors arise from metastatic primary cancers originating elsewhere in the body. The two chief sources of secondary brain tumors are lung cancer in the male and breast cancer in the female. The five year survival rate for primary brain tumors is only about thirty-five percent.

The most common therapy given to such victims is surgical resection. The normal-tumor boundaries for different primary and secondary brain tumors vary from fingerlike protrusions of tumor cells into normal tissues in glioblastoma multiforme to well-circumscribed nodules with possible surrounding edema in most secondary tumors. The most common initial therapy for primary and secondary brain tumors is surgical resection.

Many studies have shown that the degree of resection significantly influences the time to recurrence and the overall survival of brain tumor patients. Successful resection relies on complete removal of the tumor. Aggressive surgery is the brain is not acceptable, yet residual tumorous tissue left behind after resection is believed to be the main cause of morbidity.

Currently, surgical navigation systems and ultrasonography are used intraoperatively to help neurosurgeons locate brain tumor and maximize resection. Surgical navigation systems enable neurosurgeons to relate the position of a surgical instrument to structures present in preoperative computerized tomography (CT) or magnetic resonance (MR) images. However, CT or MR imaging may not delineate the exact brain tumor borders. Studies have shown that neoplastic cells can be found in brain tissue outside the apparent tumor margins defined by contrast-enhanced CT or MR imaging. More importantly, the accuracy of surgical navigation systems can be degraded by registration error and intraoperative brain deformation which may shift brain tumor borders in image space by more than a centimeter from their actual locations. Ultrasonography is able to detect brain tumors because of their hyperechoic characteristics. However, peritumoral edema is also hyperechoic, which hampers tumor and tumor margin identification. Thus, despite the applications of these technologies in neurosurgery, significant residual tumor mass is often found to be left behind in patients after craniotomy. Neurosurgeons also rely on visual inspection and/or on-site pathology to locate tumors and tumor margins. Visual inspection is subjective and often incorrect as the visual characteristics of many brain tumors mimic that of normal brain. In addition, on-site pathology is expensive and time-consuming. Hence, there is a need for an objective, intraoperative real-time system which is capable of accurately differentiating brain tumors from normal brain tissue, thus detecting tumor margins with sub-millimeter spatial resolution.

Optical spectroscopy, such as fluorescence spectroscopy, has been shown capable of detecting subtle changes in tissue architecture and biochemical composition associated with the progression of disease in near real-time. Optical spectroscopy has been successfully applied to detect disorders of various organ systems (e.g., cervix, skin, etc) both in vitro and in vivo. Several commercial systems are currently available for clinical diagnosis in the bronchus, cervix, etc. However, relatively few studies have addressed the diagnostic potential of optical spectroscopy in brain tumors. It has been reported that fluorescence peaks at 470, 520, and 630 nm emission were measured from human brain tissues in vitro at 360, 440, and 490 nm excitation, respectively. Others have observed significant differences in autofluorescence properties between normal and tumorous human brain tissues at 360 nm excitation. The results of these studies were inconclusive in terms of the effectiveness of autofluorescence spectroscopy alone for brain tumor demarcation.

Several investigators have used fluorescence dyes, such as 5-aminolevulinic (ALA), to enhance brain tumor detection. Low sensitivity of this method at the borders of infiltrating tumors has been reported as the fluorescence dye is not taken up by tumor cells where the blood brain barrier is intact. Moreover, ALA-induced fluorescence spectroscopy encounters additional problems including bleaching of fluorescence due to excessive or prolonged illumination. Consequently, dye-enhanced fluorescence spectroscopy may not be the ideal approach for brain tumor demarcation.

Diffuse reflectance spectroscopy is a fast, noninvasive method used to determine optical properties of a sample. It is typically obtained by illuminating a sample (e.g., tissue) with a broadband white light source. Because of the changes in structure and morphology at the cellular and sub-cellular level, certain optical properties of human normal brain tissues are different in certain respects from that of human brain tumorous tissues.

SUMMARY OF THE INVENTION

In one aspect, the invention is system for brain tumor margin detection comprising: a source of white light; a source of laser light at a wavelength of about 330–360 nm; a fiber optic probe coupled with the source of white light and the source of laser light so as to deliver the white light and the laser light to a working end of the probe; a spectroscope coupled with the fiber optic probe so as to receive autofluorescent and diffuse reflectance light returned from tissue contacted by the working end of the probe and provide a frequency spectrum of the returned light; a system controller including a processor coupled with the spectroscope and programmed to analyze the frequency spectrum to distinguish between light returned to the spectroscope from tumorous and from non-tumorous tissues.

BRIEF DESCRIPTION OF THE DRAWINGS

The foregoing summary, as well as the following detailed description of the presently preferred embodiments of the invention, will be better understood when read in conjunction with the appended drawings. It should be understood, however, that this invention is not limited to the precise arrangements illustrated. In the drawings which are diagrammatic:

FIG. 2a is an end view of a fiber optic probe;

FIG. 2b is a side elevation of the fiber optic probe end of FIG. 2a;

FIG. 2c is an illustration of the overlapping fields of view of the center fiber optic wave guide and a perimeter waive guide.

DETAILED DESCRIPTION OF PREFERRED EMBODIMENTS

Figure 1:
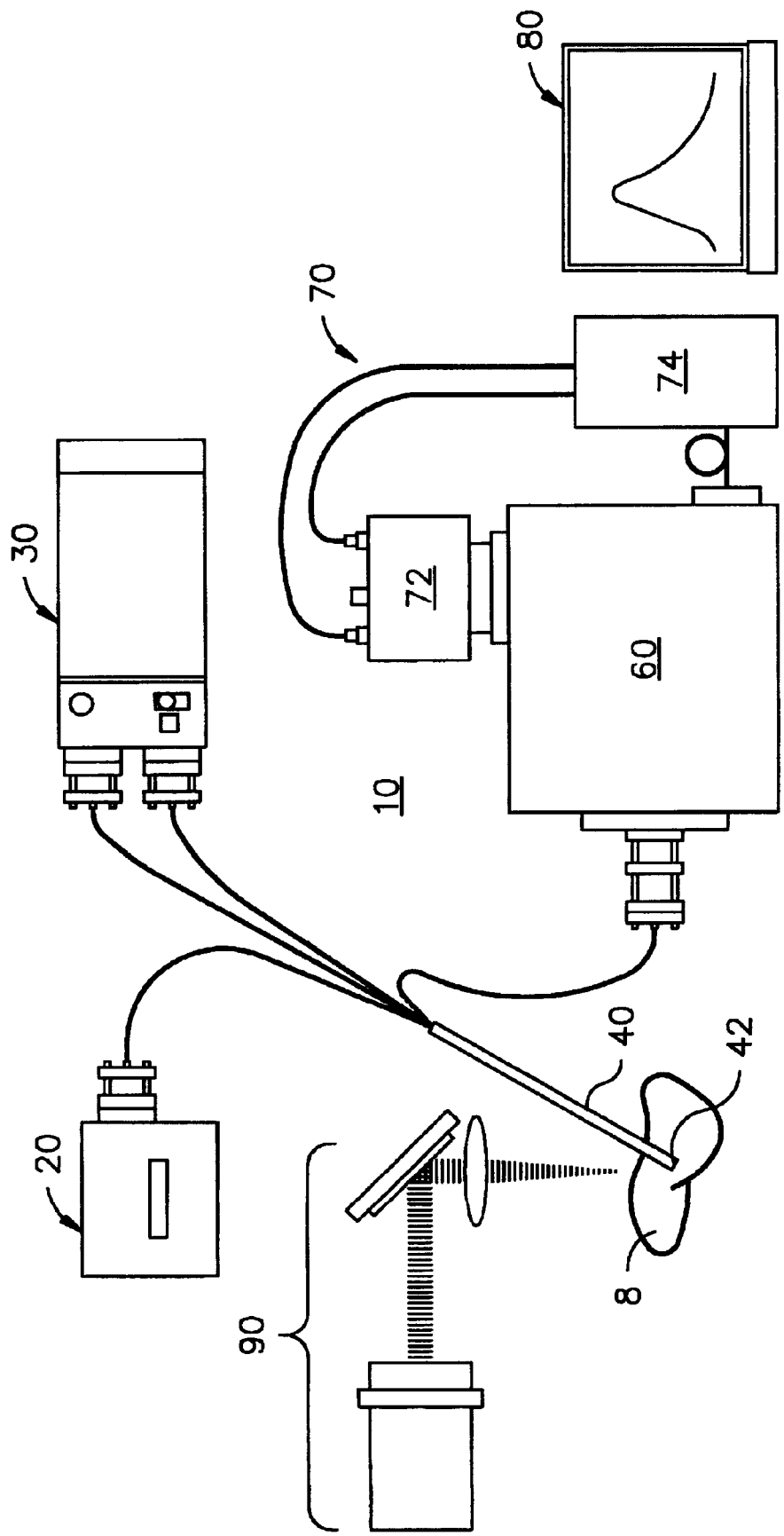
FIG. 1 is a block diagram of a tumor margin identification system of the present invention and a guided ablative laser.

In the drawings, like numerals are used to indicate like elements throughout. The present invention provides a system for tumor margin detection, specifically, in vivo brain tumor margin detection in real-time or near real time (less than one second). The components of the detection system, which is itself indicated generally at 10, are depicted in FIG. 1. They include: a source of white light 20, a source of laser light 30, a fiber optic probe 40 coupled with the source of white light 20 and the source of laser light 30 so as to deliver the white light and the laser light to a working end 42 of the probe 40; a spectrograph 60 coupled with the fiber optic probe so as to receive autofluorescent and diffuse reflectance light returned from in vivo tissue 8 contacted by the working end 42 of the probe 40 and provide a frequency spectrum of the returned light; a frequency amplitude detector 70 in the form of a CCD camera 72 with a camera controller 74, and a processor 80 in the form of a PC coupled with the spectrograph through the detector 70 and programmed to analyze the frequency spectrum of light carried from the working tip of the probe 40 to the spectrometer 60 to distinguish between light returned to the spectrograph from tumorous tissue and from non-tumorous tissue.

Fluorescence and diffuse reflectance spectra of tissue samples are measured with system 10 illustrated in FIG. 1. Suggestedly, a laser (e.g. a 337 nm high-pressure nitrogen laser from Oriel Corporation, Stratford, Conn.) is used as an excitation source for autofluorescence measurements. White light source (e.g. a 150-Watt illuminator, Fiber Lite, Model 180 from Edmund Scientific Company) emitting broadband white light from 400 nm to 850 nm is used for diffuse reflectance measurements. Light delivery and collection is preferably achieved with a 'Gaser' fiber optic probe (Visionex, Inc., Atlanta, Ga.). This probe comprises a plurality of individual wave guides, in particular seven, in the form of 300 micron core diameter glass fibers as shown in FIGS. 2a–2c. The probe can be gas or low temperature plasma sterilized. A central fiber 44a is directed conventionally, with a squared off tip. The tips of the surrounding fibers 44b–44g are shaped, in particular tapered, to optimize overlap of excitation and collection volumes as shown in FIG. 2c. Two of the surrounding fibers 44b and 44e deliver laser pulses and white light respectively to the tissue sample 8 (FIG. 1) while the remaining fibers 44a, 44c, 44d, 44f, 44g collect autofluorescence emission induced by the laser light in and diffuse reflectance generated by the white light from the tissue sample 8. An area is preferably illuminated sequentially with the laser and white light and autofluorescence and defuse reflectance gathered sequentially from the same illuminated area.

The gathered light is carried by the fiber optic probe 40 to the spectrograph 60 (e.g. a Triax 180 from Instruments S.A., Inc., Edison, N.J.) where it is dispersed and detected with detector 70, suggestedly a thermoelectrically cooled CCD camera (e.g. a Spectra One from Instruments S.A., Inc., Edison, N.J.). For fluorescence measurements, reflected laser light is suggestedly eliminated from the gathered light by filters, suggestedly two 360 nm long pass filters, placed in front of entrance slit of the spectrograph 60. The entire system 10 is preferably controlled by system controller 80 preferably including a processor such as a personal computer programmed to automatically take and analyze measurements and at least initially provide a tumor/not tumor output.

The system 10 is used as follows to identify tumorous tissue. The fiber optic probe 40 is placed directly in contact with the tissue sample 8 for each measurement Three spectra are acquired by the system controller 80 at each investigated site of brain tissue sample 8: a baseline intensity level $B(\lambda)$ (i.e., measured with no excitation light), a fluorescence spectrum $F(\lambda)$ (measured response of the tissue sample to the laser light source 30), and a reflectance spectrum $Rd(\lambda)$ (measured response to the tissue sample from the white light source 20), where ($\lambda$) is the wavelength. Currently, operating lights are pointed away from the measurement site and any room lighting directly above the patient dimmed during each measurement.

The system 10 is adjusted so as to operate uniformly from measurement to measurement. The output power of the white light source is maintained at a constant maximum level, suggestedly 30 mW for the indicated fiber light source. Laser 30 is operated at a uniform repetition rate, pulse width and average pulse energy manner (20 Hz, 5 ns and 50±5 $\mu$J for in vivo studies and 6.5 J for in vitro studies, respectively, for the above identified Oriel laser). An integration time of about 1 second or more is suggested to achieve high signal-to-noise ratio. Spectra from fluorescence and reflectance standards (i.e., $F_{ref}(\lambda)$ and $R_{ref}(\lambda)$) can be measured to monitor changes in laser pulse energy, white light power, and other instrumental parameters. The fluorescence standard might be a dilute concentration of Rhodamine 6G solution (2 mg/L) in ethylene glycol contained in a quartz cuvette. The reflectance standard might be a 20% reflectance plate (e.g. a Labsphere, North Sutton, N.H.) placed in a sealed black box.

Figure 3:
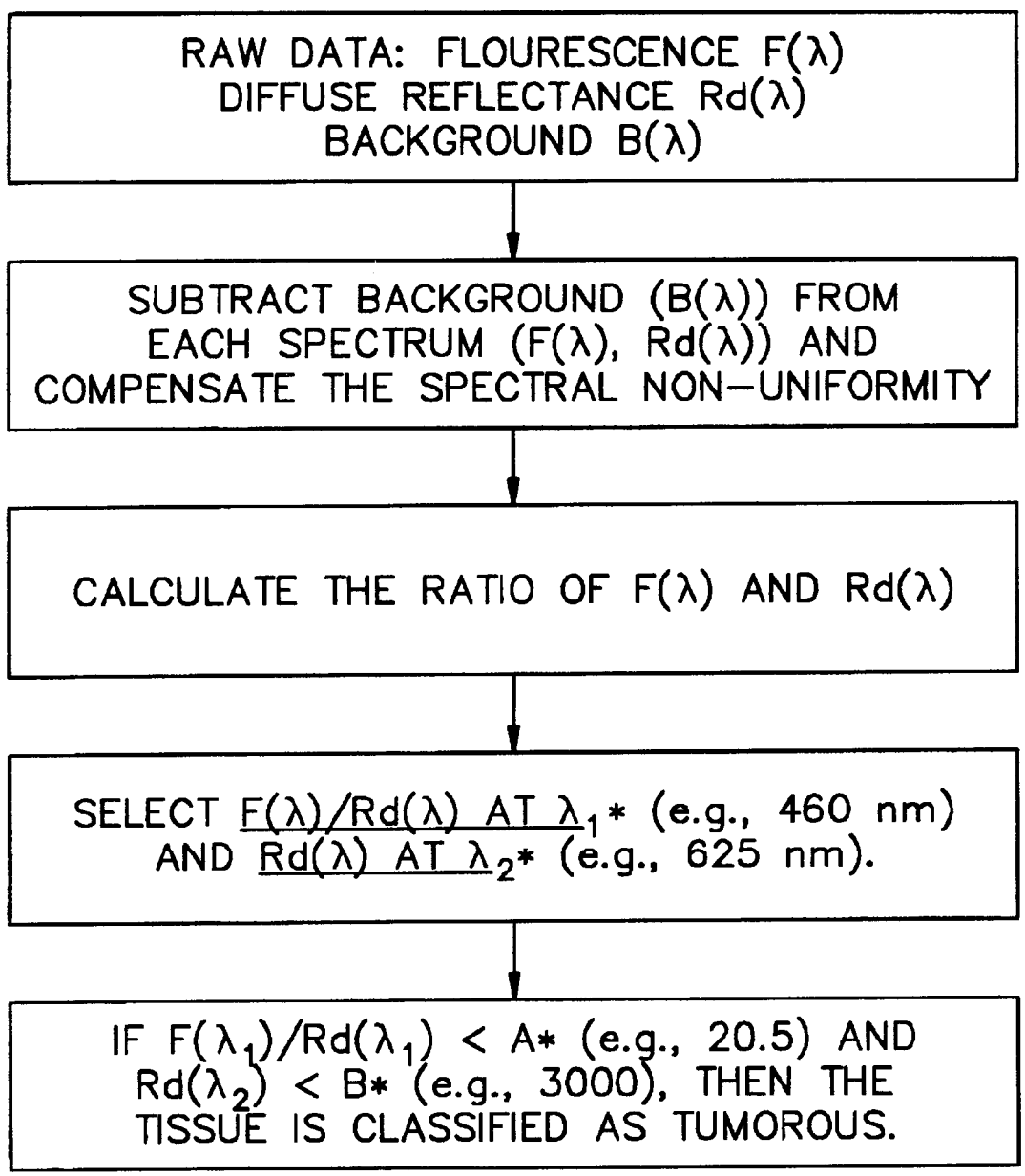
FIG. 3 if a block diagram showing the steps of data processing for tumor margin detection.

FIG. 3 depicts in diagram form the processing of the spectral data carried by the probe to the spectrograph. Spectral data is pre-processed before any analysis is conducted by the system controller 80 (e.g. the PC). Background subtraction is first performed on each selected spectrum with its corresponding baseline measurement (e.g. B (400 nm–600 nm) from F (400 nm–600 nm) and Rd (400 nm–600 nm) and B (600 nm–800 nm) from Rd (600 nm–800 nm)).

Correction factors (C) are generated by taking ratios between the standard spectra ($S(\lambda)$) measured prior to the start of the study and those acquired for every experiment of the study.

$$C_i = S_i(\lambda)/S_1(\lambda) \qquad (1)$$

where $S(\lambda) = F_{ref}(\lambda)$ or $Rd_{ref}(\lambda)$, $\lambda = 620$ nm for fluorescence, 700 nm for reflectance, i=1 to n, n is the total number of experiments.

Each correction factor $C_i$ is then multiplied to every sample spectrum acquired in a given experiment i, thus ensuring spectral intensity as valid discrimination information.

All fluorescence spectra are corrected for the non-uniform spectral response of the detection system using correction factors obtained by recording the spectrum of an National Institute of Standards and Technology (NIST) traceable calibration tungsten ribbon filament lamp. Reflectance spectra are multiplied by wavelength-dependent factors to account for non-uniform spectral response of the detection system as well as spectral emission of the reflectance light source. These factors are derived from the reflectance measurement of a mirror with a known wavelength-dependent reflectivity (e.g. a 10R08ER.1 mirror from Newport Corporation, Irvine, Calif. and are obtained before the equipment is shipped. After post-processing, changes in fluorescence and reflectance spectra, such as intensity and line shape, are correlated with histopathological identities of brain tissue sections. Empirical diagnostic algorithms are developed based on intensity, line shape, and ratio of fluorescence and diffuse reflectance spectra for separating tumorous brain tissues from normal brain tissues.

By way of background, excitation emission matrices ("EEM") were initially measured in vitro with a standard luminescence spectrometer (Model LS 50B, Perkin-Elmer Ltd., England) on human brain samples (i.e., cortex) of normal and malignant brain tissues. These initial measurements showed only two distinct fluorescence peaks: one at 290 nm excitation, 350 nm ($\pm 5$ nm) emission, and another at 330 nm excitation, 460 nm ($\pm 10$ nm) emission. Both fluorescence peaks were compared among the brain tissue samples. The intensity of the fluorescence peak at 330 nm excitation, 460 nm emission was found to be consistently lower in brain tumorous tissues than that in normal brain tissues. In addition, a small shift in peak location of this fluorescence emission was observed in brain tumors compared to normal brain tissue. These observations suggested that the fluorescence peak at 330 nm excitation, 460 nm emission would maximize the capability of brain tissue discrimination based on fluorescence. Therefore, a nitrogen laser (337 nm closest to 330 nm) was selected as the optimal laser excitation wavelength.

Then, fluorescence and diffuse reflectance spectra from 127 investigated sites in brain samples from 20 patients, including those used in the EEM study, were measured using the system described in FIG. 1. Representative fluorescence and diffuse reflectance spectra were acquired from normal human brain tissues and different types of human brain tumors. In general, the fluorescence intensity at 460 nm emission of normal gray and white matter was found to be greater than that of primary and secondary tumor tissues. This observation was consistent with that made from EEM measurements. Diffuse reflectance of most brain tissues reached the maximum around 625 nm and then decreased gradually as wavelength increased. Above 600 nm where blood absorption has the least influence, diffuse reflectance of white matter was much more intense than that of other brain tissues. However, diffuse reflectance of gray matter was similar to that of tumor tissues above 600 nm. Valleys at 415 nm, 542 nm, and 577 nm due to hemoglobin/oxyhemoglobin ($Hb/HbO_2$) absorption were clearly seen in fluorescence as well as diffuse reflectance spectra of brain tissues. No consistent differences, however, could be observed in the line shape of fluorescence and diffuse reflectance spectra between normal and malignant brain tissues.

Processed fluorescence and diffuse reflectance spectra from all brain tissues were analyzed in terms of intensities and ratios of intensities at different wavelengths to identify parameters that separate different brain tissue types. In addition, fluorescence spectra of all samples were normalized to their maximum to study the changes in line shape. Results of the analysis suggest different algorithms are required for separation of primary brain tumors and normal brain tissues as compared to secondary brain tumors and normal brain tissues.

A plot of fluorescence intensity at 460 nm emission ($F_{460}$) with respect to the diffuse reflectance intensity at 625 nm ($Rd_{625}$) for all normal tissues and primary tumor tissues indicated a clear separation between normal brain tissues and primary brain tumors along the $F_{460}$ axis but not along the $Rd_{625}$ axis. This indicates that fluorescence alone can differentiate normal brain tissues from primary brain tumors. Although reflectance spectra can be used to separate the samples based on white matter content, reflectance alone cannot separate between normal and tumor tissues. A simple one-dimensional discrimination algorithm, using a $F_{460}$ of 10000 calibrated units (c.u.) as the cutoff, yields a sensitivity and specificity of 97% and 96%, respectively, in separating primary brain tumors from normal brain tissues. Only two investigated sites in brain tumor samples and one in healthy gray matter were misclassified. The same discrimination algorithm was also applied to the secondary brain tumors. However, this algorithm only yielded a sensitivity of 67% in separating secondary brain tumors from normal brain tissues.

A different empirical discrimination algorithm was developed for discriminating secondary brain tumors from normal brain tissues using the ratio of fluorescence emission and diffuse reflectance at 460 nm ($F_{460}/Rd_{460}$) and $Rd_{625}$. A scatter plot of $F_{460}/Rd_{460}$ with respect to $Rd_{625}$ was generated for all normal brain tissue samples and secondary brain tumors. Using $F_{460}/Rd_{460}$ of 20.5 and $Rd_{625}$ of 2500 as cutoffs, this algorithm yields a sensitivity of 94% and specificity of 90% for differentiating secondary brain tumors from normal brain tissues. Only one secondary brain tumor sample was misclassified as a normal brain tissue. The same discrimination algorithm was also applied to primary brain tumors, which yields a sensitivity of 95% and specificity of 90%. Thus, the sensitivity and specificity of this algorithm for separating all brain tumors and normal brain tissues are 96% and 90%, respectively.

In vitro studies to assess the potential of optical spectroscopy for brain tumor detection, involving spectra acquired from 127 investigated sites in brain sections from 20 patients, showed that empirical discrimination algorithms with a high specificity and sensitivity can be easily developed using fluorescence at 460 nm emission and diffuse reflectance at 460 nm and 625 nm. These results attest the validity of using combined fluorescence and diffuse reflectance spectroscopy for discrimination of primary and secondary tumors from normal brain tissues.

All fluorescence spectra acquired in the in vitro study exhibited only one fluorescence peak at 460 nm ($\pm 10$ nm) emission using 337 nm excitation or longer. This observation is different from those reported previously in which multiple fluorescence peaks were measured at various excitation wavelengths. In addition, no definite change in the line shape was found between the fluorescence spectra of normal brain tissues and those of brain tumors. The fluorescence based empirical discrimination developed in this study, therefore, only utilizes the fluorescence intensity of about 460 nm emission ($F_{460}$). This discrimination algorithm performs very well in separating primary brain tumors from normal brain tissues; sensitivity of 97% and specificity of 96% are achieved. The success of this algorithm is attributed to $F_{460}$ which is consistently lower in primary brain tumors than that in normal brain tissues. However, this fluorescence based discrimination algorithm is less effective in separating secondary brain tumors from normal brain tissues due to strong $F_{460}$ from some secondary brain tumors.

To circumvent the limitation of the fluorescence based algorithm in differentiating secondary brain tumors, a second discrimination algorithm is developed based on combined fluorescence and diffuse reflectance, $F_{460}/Rd_{460}$ and $Rd_{625}$. The ratio of $F_{460}$ and $Rd_{460}$ is used to reduce fluorescence spectral distortion introduced by tissue reabsorption and scattering. $Rd_{625}$ is selected because of the differences in its intensity between different brain tissue types with minimum influence from absorption of $Hb/HbO_2$. This algorithm is effective in differentiating secondary brain tumors from normal brain tissues, with a sensitivity of 94% and specificity of 90%. It separates all brain tumors from normal brain tissue with a sensitivity and specificity of 96% and 90%. It should be noted that both algorithms were developed based on the current data set and should be considered as biased.

Tissue fluorescence intensity is determined not only by the concentration of natural fluorophores within the tissue but also by the optical properties of the tissue. Hence, interpreting changes in the fluorescence spectra of various brain tissue types is complex. It has been suggested that the concentration of many natural fluorophores, such as nicotinamide adenine dinucleotide (NADH), varies between normal and malignant tissues. In addition, increase in hemoglobin content, which leads to an increase in absorption coefficient at 337 nm as well as 460 nm, could also reduce the fluorescence intensity at 460 nm emission. While the specific cause(s) for the variations in the fluorescence intensity at 460 nm emission in the different brain tissues types is not yet known, the interdependence of tissue optics and the fluorescence emission indicates that the accuracy of a discrimination algorithm based on fluorescence intensity alone may be degraded by, for example, blood contamination.

Distinct architectural changes at the cellular and subcellular level are exhibited between normal and malignant brain tissues. For example, brain white matter is relatively anuclear but most aggressive tumors are characterized with a high density of cells (and therefore nuclei) and a higher nuclear-cytoplasmic ratio. Thus optical properties vary significantly between different brain tissue types. However, diffuse reflectance alone is insufficient for brain tissue discrimination as the level of diffuse reflectance from gray matter is very similar to those from brain tumors. This may seem incoherent with the optical properties measurements of brain tissues reported by others who found that the ratio of absorption and scattering coefficient from gray matter is lower than that from brain tumors, especially between 600 nm and 800 nm. However, it should be noted that the intensity of diffuse reflectance at a fixed radial position (Rd(r)) does not necessarily correlate linearly to the variations in absorption and scattering coefficients of tissue samples. Hence the same Rd(r) may be measured from two samples with different optical properties. This has been verified with a Monte Carlo simulation program.

In vivo data gathered thus far shows good correlation with those obtained in vitro. In particular, the $F_{460}/Rd_{460}$ Cutoff was changed to 22 and the cutoff changes to 3030 to yield a sensitivity and specificity of eighty-three percent and eighty-five percent, respectively.

Tumor ablation using a Free Electron Laser (FEL) 90 (see FIG. 1) has also been investigated. FEL is believed to be an ideal tool for removing residual tumor mass at a brain tumor boundary because it provides wavelength tunability and high precision in terms of tissue ablation. The ablation of native (normal) and tumorous brain tissue with FEL pulses of various laser parameters (e.g. energy density) was examined. Autofluorescence emission and diffuse reflectance were measured at the ablation sites before and immediately after FEL ablation. With sufficient laser energy (e.g. 70 J/sq. cm.), both 3 $\mu$m and 6 $\mu$m FEL ablated brain tissue cleanly. No sign of thermal damage (i.e. tissue whitening) was visually observed after ablation. More importantly, the autofluorescence and diffuse spectra of brain tissues within the ablation zones remained unchanged. In contrast. Ablation using FEL pulses with energy densities slightly above the ablation threshold caused significant amounts of thermal damage. This was especially noticeable for gray matter/ Significant increases in autofluorescence emission and diffuse reflectance were consistently measured from coagulated tissues after ablation. In some cases. Autofluorescence emission or diffuse reflectance from coagulated brain tissues were found to be three or four times greater than those measured from native brain tissues. It was further found that coagulated brain tissues have a much higher scattering coefficient compared to that of native brain tissues at any given wavelength in the visible light spectrum. Accordingly, FEL pulses with energy densities several times that of the ablation threshold, suggestedly at least three and preferably at least four times that of the ablation threshold (e.g., 70 J/sq.cm. or more at $\lambda$=6.4 $\mu$m) should be used to cleanly ablate the affected brain tissue without altering the spectral features of surrounding brain tissues by photocoagulation.

Referring back to FIG. 1, initially the FEL is guided manually by the surgeon in response to the tumorous/non-tumorous output of the system 10. However, it is currently envisioned that the FEL and system would be combined to use a single probe with the FEL operation being automatically controlled by the system controller.

What is claimed is:

1. A system for brain tumor margin detection comprising:
    a source of white light;
    a source of laser light at a wavelength of about 330–360 nm;
    a fiber optic probe coupled with the source of white light and the source of laser light so as to deliver the white light and the laser light to a working end of the probe;
    a spectroscope coupled with the fiber optic probe so as to receive autofluorescent and diffuse reflectance light returned from tissue contacted by the working end of the probe and provide a frequency spectrum of the returned light;
    a system controller including a processor coupled with the spectroscope and programmed to analyze a ratio of fluorescent light and diffuse reflectance light delivered to the spectrometer by the fiber optic probe to distinguish between light returned to the spectroscope from tumorous and from non-tumorous tissues.

2. The system of claim 1 wherein the processor identifies tumorous brain tissue contacted by the working end of the probe based in part upon intensity of fluorescence light at about 400–600 nm delivered to the spectrometer by the fiber optic probe.

3. The system of claim 1 wherein the processor identifies tumorous brain tissue contacted by the working end of the probe based at least in part upon intensity of diffuse reflectance light at between about 400 nm and 800 nm returned to the spectrometer by the probe.

4. The system of claim 1 wherein the processor identifies tumorous brain tissue contacted by the working end of the probe based at least in part upon the ratio of the intensity of fluorescence and diffuse reflectance light between about 400 nm and 600 nm returned to the spectrometer by the probe.

5. The system of claim 1 in combination with a free electron laser configured to be guided by the system processor.

6. The system of claim 1 wherein the system controller generates a signal representing a ratio of intensity of autofluorescent light at a first frequency obtained from an area of brain tissue illuminated in vivo by the laser light source and intensity of diffuse reflectance light at the first frequency obtained from the same area of brain tissue illuminated in vivo by the white light source.

7. The system of claim 6 wherein the first frequency is between 400 nm and 600 nm.

8. The system of claim 6 wherein the system controller generates another signal representing intensity of diffuse reflectance light at a second frequency above the first frequency and obtained from the same area brain tissue in response to the same in vivo illumination of the area of the brain tissue by the white light source.

9. The system of claim 8 wherein the second predetermined frequency is between 600 nm and 800 nm.

10. A system for brain tumor margin detection comprising:

a white light source emitting broad band light from at least 400 nm to at least 850 nm;

a laser light source emitting coherent light at a wavelength between 330 nm and 360 nm;

a fiber optic probe coupled with the white light source and the laser light source so as to deliver in vivo the white light and the laser light to an area of brain tissue proximal a working end of the probe;

a spectroscope coupled with the fiber optic probe so as to receive from the working end of the probe, autofluorescent light emitted from the area in response to illumination by the coherent light and diffuse reflectance light reflected from the same area in response to illumination by the white light; and a system controller operatively coupled with the spectroscope and configured to generate a plurality of signals, at least one signal representing a ratio of intensity of the autofluorescent light at a first wavelength obtained from the area of brain tissue in response to illumination of the area by the coherent light and intensity of the diffuse reflectance light at the same first wavelength also obtained from the same area of the brain tissue in response to illumination of the area by the white light.

11. A method of using the system of claim 10 comprising the steps of:

illuminating in vivo the area of brain tissue separately with the laser light source and the white light source:

separately gathering with the fiber optic probe, the autofluorescent light emitted in the brain tissue area in response to the laser light source and diffuse reflectance light passed through the brain tissue area illuminated by the white light source;

generating the signal representing the ratio of intensity of the autofluorescent light at the first wavelength and intensity of the diffuse reflectance light at the same first wavelength; and comparing magnitude of the ratio signal to a predetermined magnitude value to determine in vivo tumor presence in the illuminated brain tissue area.

12. The method of claim 11 further comprising the step of calibrating the autofluorescent light against an independent standard before the using step.

13. The method of claim 11 further comprising the step of calibrating the diffuse reflectance light against an independent standard before the using step.

14. A system for brain tumor margin detection comprising:

means for illuminating in vivo brain tissue with electromagnetic radiation at optical wavelengths;

means for collecting electromagnetic radiation at optical wavelengths returned from the illuminated in vivo brain tissue;

means for correcting intensities of the collected electromagnetic radiation at at least one wavelength for nonuniform spectral response of the system; and means responsive to the corrected intensities for generating diagnostic signals indicative of histopathological characteristics of the illuminated brain tissue.

15. The system of claim 14 wherein at least one of the generated diagnostic signals represents a ratio of intensity of autofluorescence emitted in vivo from an illuminated area of the brain tissue and intensity of diffuse reflectance from the same area of the brain tissue illuminated with white light.

16. The system of claim 15 wherein the at least one generated diagnostic signal represents the ratio of autofluorescence intensity at a first wavelength and diffuse reflectance intensity at the same first wavelength.

17. The system of claim 16 wherein the first wavelength is in the range of 400 nm to 600 nm.

18. The system of claim 17 wherein the first wavelength is about 460 nm.

19. A method of using the system of claim 14 comprising the steps of:

illuminating in vivo an area of brain tissue with the electromagnetic radiation;

collecting electromagnetic radiation returned from the illuminated in vivo area of brain tissue;

correcting intensities of at least a plurality of wavelengths of the electromagnetic radiation collected from the illuminated area of the brain tissue using independent intensity standards; and using the corrected wavelength intensities to identify brain tumor presence in the illuminated area of in vivo brain tissue.

20. The method of claim 19 wherein the using step comprises the step of generating a ratio of corrected intensity of autofluorescent light emitted in vivo by the illuminated area of the brain and corrected intensity of diffuse reflectance of white light in the illuminated area of the brain.

* * * * *

UNITED STATES PATENT AND TRADEMARK OFFICE
CERTIFICATE OF CORRECTION

PATENT NO. : 6,377,841 B1
DATED : April 23, 2002
INVENTOR(S) : Wei Chiang Lin

It is certified that error appears in the above-identified patent and that said Letters Patent is hereby corrected as shown below:

Column 1,
Line 12, before the heading, BACKGROUND OF THE INVENTION, insert the following heading and section:
-- STATEMENT REGARDING FEDERALLY SPONSORED RESEARCH OR DEVELOPMENT
This invention was produced, in part, using funds obtained through grant number 1R01CA085989-01A1 from the National Institutes of Health and grant number N000149411023 from the Office of Naval Research. Consequently, the federal government has certain rights in this invention. --

Signed and Sealed this

Twenty-third Day of July, 2002

*Attest:*

*Attesting Officer*

JAMES E. ROGAN
*Director of the United States Patent and Trademark Office*